United States Patent [19]
Sun

[11] Patent Number: 6,005,155
[45] Date of Patent: Dec. 21, 1999

[54] MODIFICATION OF MOLECULAR SIEVE CATALYST FOR REDUCED METHANE PRODUCTION DURING CONVERSION OF OXYGENATES TO OLEFINS

[75] Inventor: Hsiang-ning Sun, Houston, Tex.

[73] Assignee: Exxon Chemicals Patents Inc., Houston, Tex.

[21] Appl. No.: 08/984,667

[22] Filed: Dec. 3, 1997

[51] Int. Cl.$^6$ .............................. C07C 1/00; B01J 29/04
[52] U.S. Cl. ...................... 585/640; 585/638; 585/639; 502/85
[58] Field of Search .................................. 585/638, 639, 585/640; 502/85

[56] References Cited

U.S. PATENT DOCUMENTS

| | | | |
|---|---|---|---|
| 4,062,905 | 12/1977 | Chang et al. ............................ | 260/682 |
| 4,296,266 | 10/1981 | Wunder et al. ......................... | 585/640 |
| 4,440,871 | 4/1984 | Lok et al. ............................... | 502/214 |
| 4,471,150 | 9/1984 | Wu .......................................... | 585/640 |
| 4,481,376 | 11/1984 | Wunder et al. ......................... | 585/640 |
| 4,605,809 | 8/1986 | Litterer et al. .......................... | 585/640 |
| 5,234,872 | 8/1993 | Apelian et al. ......................... | 502/62 |

FOREIGN PATENT DOCUMENTS

| | | |
|---|---|---|
| 254530 | 12/1986 | Germany . |
| WO 93/24430 | 12/1993 | WIPO . |
| WO 97/21652 | 6/1997 | WIPO . |

OTHER PUBLICATIONS

Zeolites, vol. 17, pp. 212–222 (1996).
B. Kraushaar–Czarnetzki, et al., "Isomorphous Substitution and the Generation of Catalytic Activity in VPI–5," Journal of Catalysis vol. 141, pp. 140–147 (1993).

*Primary Examiner*—Walter D. Griffin
*Assistant Examiner*—In Suk Bullock
*Attorney, Agent, or Firm*—Bladley A. Keller

[57] ABSTRACT

A method for modifying a molecular sieve catalyst to reduce methane production during conversion of oxygenates to olefins. The molecular sieve catalyst comprises a separately synthesized framework comprising a material selected from the group consisting of silica, alumina, phosphate, and combinations thereof. The framework is contacted with a modifier, in the absence of a salt comprising a metal selected from the group consisting of manganese, zirconium, and hafnium, under conditions effective to modify the framework but insufficient to dealuminize or deironize the framework. The modifier comprises an oxygenated chelating agent comprising a parent compound which is readily removable from the framework by calcination to leave the modified molecular sieve catalyst. Also encompassed are the modified molecular sieve catalysts produced by the method, and a method of using the modified molecular sieve catalysts to reduce methane production during conversion of oxygenates to olefins.

17 Claims, No Drawings

6,005,155

MODIFICATION OF MOLECULAR SIEVE CATALYST FOR REDUCED METHANE PRODUCTION DURING CONVERSION OF OXYGENATES TO OLEFINS

FIELD OF THE INVENTION

The present invention is directed to a method for modifying molecular sieve catalysts, to the molecular sieve catalysts produced by such method, and to a method for using the modified molecular sieve catalysts to reduce methane production during the conversion of oxygenates to olefins.

BACKGROUND OF THE INVENTION

Light olefins (defined as "ethylene, propylene, and butylene") serve as feeds for the production of numerous chemicals. Light olefins traditionally are produced by petroleum cracking. Because of the limited supply and/or the high cost of petroleum sources, the cost of producing olefins from petroleum sources has increased steadily.

Alternative feedstocks for the production of light olefins are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

The catalysts used to promote the conversion of oxygenates to olefins are molecular sieve catalysts. Because ethylene and propylene (herein defined as "light olefins") are the most sought after products of such a reaction, research has focused on what catalysts are most selective to light olefins. Methods also are needed for reducing the production of unwanted by-products, such as methane.

SUMMARY OF THE INVENTION

The present invention provides a method for modifying a molecular sieve catalyst to reduce methane production during conversion of oxygenates to olefins. The method comprises: providing a separately synthesized framework comprising a material selected from the group consisting of silica, alumina, phosphate, and combinations thereof, contacting the separately synthesized microporous framework with a modifier, in the absence of a salt comprising a metal selected from the group consisting of manganese, zirconium, and hafnium, under conditions effective to modify the framework but insufficient to perform a function selected from the group consisting of dealuminizing and deironizing the framework; wherein the modifier comprises an oxygenated chelating agent comprising a parent compound which is readily removable from the framework by calcination to leave the modified molecular sieve catalyst.

DETAILED DESCRIPTION OF THE INVENTION

In the conversion of oxygenates to light olefins (defined herein as ethylene and propylene), it is desirable to maximize the production of light olefins and to minimize the production of undesired by-products, such as methane, ethane, propane, carbon dioxide, hydrogen gas, and $C_4+$ materials, including aromatics. The present invention minimizes the production of methane during such conversion by contacting the molecular sieve catalyst used to promote the conversion with a modifier comprising an oxygenated chelating agent comprising a parent compound which is readily removable from the framework by calcination.

Molecular sieve catalysts generally comprise a crystalline, three dimensional, stable framework enclosing cavities of molecular dimensions. The cavities form a well-defined microporous system of channels and cages. The cavities or "pores" in a given type of molecular sieve have well-defined dimensions which will only allow molecules up to a certain size to enter the pores.

The present invention should reduce the production of methane by substantially any molecular sieve catalyst, regardless of pore size. Preferred molecular sieve catalysts for modification according to the present invention are "small" and "medium" pore molecular sieve catalysts. "Small pore" molecular sieve catalysts are defined as catalysts with pores having a diameter of less than about 5.0 Angstroms. "Medium pore" molecular sieve catalysts are defined as catalysts with pores having a diameter in the range of from about 5 to about 10 Angstroms.

One group of suitable molecular sieve catalysts is the zeolite group. Several types of zeolites exist, each of which exhibit different properties and different utilities. Structural types of zeolites that are suitable for use in the present invention with varying levels of effectiveness include, but are not necessarily limited to AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO and substituted examples of these structural types, as described in W. M. Meier and D. H. Olsen, *Atlas of Zeolite Structural Types* (Butterworth Heineman-3rd ed. 1997), incorporated herein by reference. Structural types of medium pore molecular sieves useful in the present invention include, but are not necessarily limited to, MFI, MEL, MTW, EUO, MTT, HEU, FER, AFO, AEL, TON, and substituted examples of these structural types, as described in the *Atlas of Zeolite Types,* previously incorporated herein by reference.

Preferred zeolite catalysts for use in the present invention include, but are not necessarily limited to, ZSM-5, ZSM-34, erionite, and chabazite.

Silicoaluminophosphates ("SAPO's") are another group of molecular sieve catalysts that are useful in the invention. SAPO's have a three-dimensional microporous crystal framework of $PO_2^+$, $AlO_2-$, and $SiO_2$ tetrahedral units. Suitable SAPO's for use in the invention include, but are not necessarily limited to SAPO-34, SAPO-17, and SAPO-18. A preferred SAPO is SAPO-34, which may be synthesized according to U.S. Pat. No. 4,440,871, incorporated herein by reference, and *Zeolites,* Vol. 17, pp. 512–522 (1996), incorporated herein by reference.

SAPO's with added substituents also may be useful in the present invention. These substituted SAPO's form a class of molecular sieves known as "MeAPSO's." Substituents may include, but are not necessarily limited to nickel, cobalt, strontium, barium, and calcium.

The molecular sieve catalysts comprise a separately synthesized framework which is modified by contact with an oxygenated chelating agent. Substantially any oxygenated chelating agent should operate in the present invention. Preferred oxygenated chelating agents comprise functional groups selected from the group consisting of an anhydride, a plurality of carboxyl groups, a combination of a hydroxyl group and a carboxyl group, and salts of said functional groups. Most preferred modifiers are selected from the group consisting of oxalic acid, maleic acid, maleic anhydride, glutaric acid, glutaric anhydride, adipic acid, EDTA, o-phthalic acid, o-phthalic anhydride, terephthalic acid, salycic acid, tartaric acid, salts thereof, and combinations thereof.

The framework of the molecular sieve catalyst may be modified using a number of different methods that are readily recognized by persons of ordinary skill in the art. Examples are static methods, batch methods, continuous methods, semi-continuous methods, and others. Given the particular method to be used and the molecular sieve to be treated, persons of ordinary skill in the art would be able to determine the optimal time and temperature to be used at a given concentration of agent and pressure.

In a preferred method, a suitable modifier should be dissolved in a suitable solvent. The solvent may be water, an organic solvent, or a mixed solvent, the only limitation being that the modifier must be soluble in the solvent under the treatment conditions. Supercritical states of certain solvents, such as water, also may be used, subject to the same limitation. The pH of the solution should be maintained in the range of from about 12 to about 1. When water is used as the primary solvent, it is advantageous to have a pH value smaller than 7 and larger than about 2.

The solution should be stirred with the separately synthesized microporous framework for a period of time in the range of from about 1 minute to about 24 hours at a temperature in the range of from about 0° C. to about 80° C., preferably in the range of from about 2 hours to about 24 hours at room temperature. If a supercritical solvent is used, the temperature and pressure must be sufficient to maintain such a state. The amount of stirring time required will depend upon the modifier.

The solid phase should be isolated using any suitable means, preferably by centrifugation or drying. If centrifugation is used, the residual solid should be washed, preferably with distilled water, and dried. Drying at a temperature in the range of from about 90° C. to about 150° C., preferably at about 100° C., for a time in the range of from about 1 hour to about 10 hours, preferably about 2 hours, should be sufficient. If drying is used, the resulting mixture should be dried for an amount of time sufficient to produce a dry powder. In a preferred embodiment, the mixture is dried at a temperature of about 110° C. for about two hours.

The resulting powder should be calcined for a period of time in the range of from about 2 hours to about 48 hours, preferably for about 16 hours, at a temperature in the range of from about 300° C. to about 800° C., preferably in the range of from about 350° C. to about 650° C., most preferably in the range of from about 550° C. to about 650° C. The resulting powder may be pressed into pellets and then crushed and sieved to a mesh size preferably in the range of from about 14 to about 20. In a preferred embodiment, the pellets are formed by application of about 137.89521 MPa (20,000 psi) of pressure.

The process for converting oxygenates to olefins employs an organic starting material (feedstock) preferably comprising "oxygenates." As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof The aliphatic moiety preferably should contain in the range of from about 1 to about 10 carbon atoms and more preferably in the range of from about 1 to about 4 carbon atoms. Representative oxygenates include, but are not necessarily limited to, lower straight chain or branched aliphatic alcohols, their unsaturated counterparts, and their nitrogen, halogen and sulfur analogues. Examples of suitable compounds include, but are not necessarily limited to: methanol; ethanol; n-propanol; isopropanol; $C_4$–$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; n-alkyl amines, n-alkyl halides, n-alkyl sulfides having n-alkyl groups of comprising the range of from about 3 to about 10 carbon atoms; and mixtures thereof As used herein, the term "oxygenate" designates only the organic material used as the feed. The total charge of feed to the reaction zone may contain additional compounds such as diluents.

Preferably, the oxygenate feedstock should be contacted in the vapor phase in a reaction zone with the defined molecular sieve catalyst at effective process conditions so as to produce the desired olefins, i.e., an effective temperature, pressure, WHSV (Weight Hourly Space Velocity) and, optionally, an effective amount of diluent, correlated to produce olefins. Alternately, the process may be carried out in a liquid or a mixed vapor/liquid phase. When the process is carried out in the liquid phase or a mixed vapor/liquid phase, different conversions and selectivities of feedstock-to-product may result depending upon the catalyst and reaction conditions.

The temperature employed in the conversion process may vary over a wide range depending, at least in part, on the selected catalyst. Although not limited to a particular temperature, best results will be obtained if the process is conducted at temperatures in the range of from about 200° C. to about 700° C., preferably in the range of from about 250° C. to about 600° C., and most preferably in the range of from about 300° C. to about 500° C. Lower temperatures generally result in lower rates of reaction, and the formation of the desired light olefin products may become markedly slow. However, at higher temperatures, the process may not form an optimum amount of light olefin products, and the coking rate may become too high.

Light olefin products will form—although not necessarily in optimum amounts—at a wide range of pressures, including but not limited to autogeneous pressures and pressures in the range of from about 0.1 kPa to about 100 MPa,. A preferred pressure is in the range of from about 6.9 kPa to about 34 MPa, most preferably in the range of from about 48 kPa to about 0.34 MPa. The foregoing pressures are exclusive of diluent, if any is present, and refer to the partial pressure of the feedstock as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction cycle time may vary from tenths of seconds to a number of hours. The reaction cycle time is largely determined by the reaction temperature, the pressure, the catalyst selected, the weight hourly space velocity, the phase (liquid or vapor), and the selected process design characteristics.

A wide range of weight hourly space velocities (WHSV), defined as weight feed per hour per weight of catalyst, for the feedstock will function in the present invention. The WHSV generally should be in the range of from about 0.01 hr$^{-1}$ to about 5000 hr$^{-1}$, preferably in the range of from about 0.1 hr$^{-1}$ to about 2000 hr$^{-1}$, and most preferably in the range of from about 1 hr$^{-1}$ to about 1000 hr$^{-1}$. The catalyst may contain other materials which act as inerts, fillers, or binders; therefore, the WHSV is calculated on the weight basis of oxygenate and catalyst.

One or more diluents may be fed to the reaction zone with the oxygenates, such that the total feed mixture comprises diluent in a range of from about 1 mol % and about 99 mol %. Diluents which may be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Preferred diluents are water and nitrogen.

A preferred embodiment of a reactor system for the present invention is a circulating fluid bed reactor with continuous regeneration, similar to a modem fluid catalytic cracker. Fixed beds can be used, but are not ideal for the process because oxygenate to olefin conversion is a highly exothermic process which requires several stages with intercoolers or other cooling devices. The reaction also results in a high pressure drop due to the production of low pressure, low density gas. Moving beds also may be used.

The invention will be better understood with reference to the following examples which are intended to illustrate, but not to limit the present invention.

EXAMPLE I

A solution was prepared by dissolving 1.019 g of ethylenediaminetetraacetic acid (EDTA) in a mixture of 25.0 cc of distilled water and 1.0 cc of commercial 28% ammonium hydroxide at room temperature. To this solution was added 4.2218 g of SAPO-34 powder, obtained from UOP, Des Plaines, Ill. The resulting mixture was stirred for 24 hours at ambient temperature, followed by washing with 20 cc of deionized water. The washing was repeated four more times. The product was dried at 110° C. for two hours. This dried powder was then calcined at 550° C. for 16 hours. The powder was pressed under 20,000 psi to form pellets which were crushed and sieved to 14–20 mesh size.

EXAMPLE II

Samples of 5 cc (approximately 2.7 grams) each of the SAPO-34 catalyst obtained from UOP, and the SAPO-34 catalyst prepared in each of Examples I and II, were mixed with 15 cc of 3 mm quartz beads and loaded into ¾" outer diameter 316 stainless steel tubular reactors which were heated by a three zone electric furnace. The first zone, acting as the preheating zone, vaporized the feed. The temperature of the center zone of the furnaces was adjusted to 450° C. and the exit pressure was maintained at 1.5 psig (112 kPa). The bottom zone temperature was set high enough to ensure that the effluent from the reactor remained in the vapor state. The reactors were first purged with nitrogen at 50 cc/min flow rate for 30 minutes. The feed to each reactor was a 4:1 ratio mixture of distilled water to methanol, respectively. The feed was pumped into the reactors and calibrated to give a flow rate of about 0.8 h$^{-1}$ WHSV. The effluents were analyzed at pre-determined intervals by on-line gas chromatographs fitted with both thermal conductivity detectors and flame ionization detectors. The following were the results.

| Catalyst | $C_2^=$ (wt %) | $C_3^=$ (wt %) | $C_2^= + C_3^=$ (wt %) | Methane (wt %) |
|---|---|---|---|---|
| SAPO-34 | 49.2 | 34 | 83.2 | 4 |
| SAPO-34-EDTA (EX. I) | 50.4 | 36.6 | 87.0 | 1.8 |
| SAPO-34 | 54.3 | 34.8 | 88.1 | 3.0 |
| SAPO-34-EDTA (EX. II) | 50.4 | 36.6 | 87.0 | 1.8 |

EXAMPLE III 1.024 g of salicylic acid (99%) was dissolved in a mixture of 20.0 cc of methanol. To this solution was added 5.02 g of SAPO-34, which was obtained from UOP. The resulting mixture was stirred for 2 hours at ambient temperature, followed by washing with 20 cc of methanol. The washing was repeated two more times. The product was dried at 110° C. for two hours. This dried powder was then calcined at 550° C. for 16 hours. The powder was pressed under 20,000 psi to form pellets, which were crushed and sieved to 14–20 mesh size. The resulting pellets were subjected to the procedure set forth in Example III with comparable results.

The foregoing results demonstrate that modification of the SAPO-34 catalyst using the oxygenated chelating agents EDTA and salicylic acid reduced the production of methane, while the overall yield of ethylene and propylene (wt %) remained approximately the same.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A method for reducing methane production during conversion of an oxygenate to olefins, said method comprising:

contacting a feed comprising said oxygenate with a modified molecular sieve catalyst under conditions effective to produce olefins;

wherein said modified molecular sieve catalyst comprises a separately synthesized microporous framework comprising a material selected from the group consisting of silicon, aluminum, phosphate, and combinations thereof; and, wherein said separately synthesized microporous framework undergoes modification by contact with a modifier in the absence of a salt comprising a metal selected from the group consisting of manganese, zirconium, and hafnium, under conditions effective to produce a modified framework but insufficient to perform either function selected from the group consisting of dealuminizing and deironizing said framework;

wherein said modified framework comprises an amount of an oxygenated chelating agent comprising a parent compound which is readily removed from said framework by calcination; and wherein, absent said modification said framework produces a first quantity of methane during said contacting, and after said modification said modified framework produces a second quantity of methane during said contacting, said second quantity of methane being less than said first quantity of methane.

2. The method of claim 1 wherein said oxygenated chelating agent comprises functional groups selected from the group consisting of an anhydride, a plurality of carboxyl groups, a combination of a hydroxyl group and a carboxyl group, and salts of said functional groups.

3. The method of claim 2 wherein said microporous framework comprises pores consisting essentially of a diameter in the range of from about 5 to about 10 Angstroms.

4. The method of claim 2 wherein said microporous framework comprises pores consisting essentially of a diameter less than about 5 Angstroms.

5. The method of claim 4 wherein said molecular sieve catalyst is a silicoaluminophosphate catalyst.

6. The method of claim 1 wherein said modifier is selected from the group consisting of oxalic acid, maleic acid, maleic anhydride, glutaric acid, glutar anhydride, adipic acid, EDTA, o-phthalic acid, o-pht tartaric acid, salts thereof, and combinations thereof.

7. The method of claim 1 wherein said microporous framework comprises pores consisting essentially of a diameter in the range of from about 5 to about 10 Angstroms.

8. The method of claim 1 wherein said microporous framework comprises pores consisting essentially of a diameter less than about 5 Angstroms.

9. The method of claim 8 wherein said molecular sieve catalyst is a silicoaluminophosphate catalyst.

10. A method for reducing methane production during conversion of an oxygenate to olefins, said method comprising:
   contacting a feed comprising said oxygenate with a modified molecular sieve catalyst under conditions effective to produce olefins;
   wherein said modified molecular sieve catalyst comprises
      a separately synthesized microporous framework comprising a material selected from the group consisting of silicon, aluminum, phosphate, and combinations thereof; and,
      functional groups selected from the group consisting of oxygenated chelating functional groups and derivatives thereof, incorporated onto said separately synthesized microporous framework in an amount sufficient to reduce methane production during conversion of said oxygenate to olefins, wherein materials incorporated onto said synthesized microporous framework comprise materials other than those selected from the group consisting of manganese, zirconium, and hafnium.

11. The method of claim 10 wherein said oxygenated chelating agent comprises functional groups selected from the group consisting of an anhydride, a plurality of carboxyl groups, a combination of a hydroxyl group and a carboxyl group, and salts of said functional groups.

12. The method of claim 11 wherein said microporous framework comprises pores consisting essentially of a diameter in the range of from about 5 to about 10 Angstroms.

13. The method of claim 11 wherein said microporous framework comprises pores consisting essentially of a diameter less than about 5 Angstroms.

14. The method of claim 13 wherein said molecular sieve catalyst is a silicoaluminophosphate catalyst.

15. The method of claim 10 wherein said microporous framework comprises pores consisting essentially of a diameter in the range of from about 5 to about 10 Angstroms.

16. The method of claim 10 wherein said microporous framework comprises pores consisting essentially of a diameter less than about 5 Angstroms.

17. The method of claim 16 wherein said molecular sieve catalyst is a silicoaluminophosphate catalyst.

* * * * *